United States Patent
Ben-David et al.

(10) Patent No.: US 12,397,149 B2
(45) Date of Patent: *Aug. 26, 2025

(54) SYSTEM AND METHOD FOR TREATING VARIOUS NEUROLOGICAL DISORDERS USING SYNCHRONIZED NERVE ACTIVATION

(71) Applicant: CogniGuard Medical Holdings Limited, Nicosia (CY)

(72) Inventors: Tamir Ben-David, Tel-Aviv (IL); Nimrod Kadim, Modiln (IL); Shmuel Glasberg, Herzliya (IL); Ra'anan Gefen, Reut (IL)

(73) Assignee: CogniGuard Medical Holdings Limited, Nicosia (CY)

( * ) Notice: Subject to any disclaimer, the term of this patent is extended or adjusted under 35 U.S.C. 154(b) by 0 days.

This patent is subject to a terminal disclaimer.

(21) Appl. No.: 18/197,756

(22) Filed: May 16, 2023

(65) Prior Publication Data

US 2023/0355960 A1    Nov. 9, 2023

Related U.S. Application Data

(63) Continuation of application No. 17/080,878, filed on Oct. 27, 2020, now Pat. No. 11,684,771, which is a
(Continued)

(51) Int. Cl.
*A61N 1/04* (2006.01)
*A61B 5/00* (2006.01)
(Continued)

(52) U.S. Cl.
CPC ............ *A61N 1/0456* (2013.01); *A61B 5/002* (2013.01); *A61B 5/0205* (2013.01);
(Continued)

(58) Field of Classification Search
CPC .. A61N 1/0456; A61N 1/0472; A61N 1/0484; A61N 1/36025; A61N 1/36031;
(Continued)

(56) References Cited

U.S. PATENT DOCUMENTS 6,684,105 B2    1/2004  Cohen et al.
8,506,469 B2    8/2013  Dietrich et al.
(Continued)

FOREIGN PATENT DOCUMENTS

WO   WO 2015/049613    4/2015
WO   WO 2017/115368    7/2017

OTHER PUBLICATIONS

Final Official Action Dated Jan. 24, 2023 from the US Patent and Trademark Office Re. U.S. Appl. No. 17/080,878. (12 pages).
(Continued)

*Primary Examiner* — Jon Eric C Morales

(57) ABSTRACT

A neuromodulation system for treatment of physiological disorders. The system includes one or more stimulators for stimulating one or more cranial nerves; one or more detectors configured for detecting a predetermined physiological state; and a control unit that controls nerve stimulation by the one or more stimulators so that it is synchronized with the at least one predetermined physiological state detected by the one or more detectors. A method of neuromodulating a patient for treatment of physiological disorder. The method includes the steps of detecting a predetermined physiological state and applying stimulation to one of the cranial nerves during the predetermined physiological state by one or more stimulators of a neuromodulation system.

22 Claims, 10 Drawing Sheets

Related U.S. Application Data continuation of application No. 16/066,335, filed as application No. PCT/IL2016/051394 on Dec. 28, 2016, now Pat. No. 10,835,735.

(60) Provisional application No. 62/271,664, filed on Dec. 28, 2015.

(51) Int. Cl.

| | | |
|---|---|---|
| *A61B 5/0205* | (2006.01) | |
| *A61H 23/02* | (2006.01) | |
| *A61N 1/05* | (2006.01) | |
| *A61N 1/36* | (2006.01) | |
| *A61B 5/024* | (2006.01) | |
| *A61B 5/0245* | (2006.01) | |
| *A61B 5/11* | (2006.01) | |
| *A61B 5/16* | (2006.01) | |
| *A61B 5/291* | (2021.01) | |
| *A61B 5/369* | (2021.01) | |
| *A61N 5/06* | (2006.01) | |

(52) U.S. Cl.
CPC .......... *A61B 5/4812* (2013.01); *A61B 5/4836* (2013.01); *A61H 23/02* (2013.01); *A61N 1/0472* (2013.01); *A61N 1/0484* (2013.01); *A61N 1/0534* (2013.01); *A61N 1/36021* (2013.01); *A61N 1/36025* (2013.01); *A61N 1/36031* (2017.08); *A61N 1/36036* (2017.08); *A61N 1/36053* (2013.01); *A61N 1/36078* (2013.01); *A61N 1/36082* (2013.01); *A61N 1/36092* (2013.01); *A61N 1/36096* (2013.01); *A61N 1/36135* (2013.01); *A61B 5/0031* (2013.01); *A61B 5/02416* (2013.01); *A61B 5/0245* (2013.01); *A61B 5/1118* (2013.01); *A61B 5/163* (2017.08); *A61B 5/165* (2013.01); *A61B 5/168* (2013.01); *A61B 5/291* (2021.01); *A61B 5/369* (2021.01); *A61B 5/4082* (2013.01); *A61B 5/4088* (2013.01); *A61B 5/6815* (2013.01); *A61B 5/6892* (2013.01); *A61B 2560/0219* (2013.01); *A61H 2201/0157* (2013.01); *A61H 2201/0207* (2013.01); *A61H 2201/0214* (2013.01); *A61H 2201/165* (2013.01); *A61H 2201/5097* (2013.01); *A61H 2205/04* (2013.01); *A61H 2205/06* (2013.01); *A61H 2205/12* (2013.01); *A61H 2230/045* (2013.01); *A61H 2230/065* (2013.01); *A61N 1/36034* (2017.08); *A61N 1/36067* (2013.01); *A61N 1/36075* (2013.01); *A61N 1/36139* (2013.01); *A61N 1/3614* (2017.08); *A61N 1/36167* (2013.01); *A61N 5/0622* (2013.01)

(58) Field of Classification Search
CPC .............. A61N 1/0534; A61N 1/36021; A61N 1/36034; A61N 1/36036; A61N 1/36053; A61N 1/36067; A61N 1/36075; A61N 1/36078; A61N 1/36082; A61N 1/36092; A61N 1/36096; A61N 1/36135; A61N 1/36139; A61N 1/3614; A61N 1/36167; A61N 5/0622; A61N 1/0452; A61N 1/0526; A61N 1/0541; A61B 2560/0219; A61B 5/002; A61B 5/0031; A61B 5/0205; A61B 5/02416; A61B 5/0245; A61B 5/1118; A61B 5/163; A61B 5/165; A61B 5/168; A61B 5/291; A61B 5/369; A61B 5/4082; A61B 5/4088; A61B 5/4812; A61B 5/4836; A61B 5/6815; A61B 5/6892

See application file for complete search history.

(56) References Cited

U.S. PATENT DOCUMENTS

| | | | |
|---|---|---|---|
| 10,232,178 | B2 | 3/2019 | Simon |
| 10,835,735 | B2 * | 11/2020 | Ben-David ........ A61N 1/36031 |
| 11,684,771 | B2 * | 6/2023 | Ben-David .......... A61N 1/0534 607/45 |
| 2003/0195588 | A1 | 10/2003 | Fischell |
| 2005/0283039 | A1 | 12/2005 | Cornel |
| 2008/0051852 | A1 | 2/2008 | Dietrich et al. |
| 2008/0249594 | A1 | 10/2008 | Dietrich et al. |
| 2014/0277255 | A1 | 9/2014 | Sabesan |
| 2015/0306392 | A1 | 10/2015 | Sabesan |
| 2019/0001117 | A1 | 1/2019 | Ben-David et al. |
| 2021/0038880 | A1 | 2/2021 | Ben-David et al. |

OTHER PUBLICATIONS

International Preliminary Report on Patentability Dated Jul. 3, 2017 From the International Bureau of WIPO Re. Application No. PCT/IL2016/051394. (7 Pages).
International Search Report and the Written Opinion Dated Apr. 25, 2017 From the International Searching Authority Re. Application No. PCT /IL20 16/0513 94. (16 Pages).
Interview Summary Dated Dec. 16, 2022 from the US Patent and Trademark Office Re. U.S. Appl. No. 17/080,878. (2 pages).
Notice of Allowance Dated Mar. 6, 2023 from the US Patent and Trademark Office Re. U.S. Appl. No. 17/080,878. (6 pages).
Notice of Allowance Dated Jul. 14, 2020 From the US Patent and Trademark Office Re. U.S. Appl. No. 16/066,335. (11 Pages).
Official Action Dated Dec. 26, 2019 From the US Patent and Trademark Office Re. U.S. Appl. No. 16/066,335. (14 Pages).
Official Action Dated Oct. 26, 2022 from the US Patent and Trademark Office Re. U.S. Appl. No. 17/080,878. (13 pages).
Vargas-Caballero et al. "Vagus Nerve Stimulation as a Potential Therapy in Early Alzheimer's Disease: A Review", Frontiers in Human Neuroscience, 16: 866434-1-866434-9, Apr. 29, 2022.

* cited by examiner

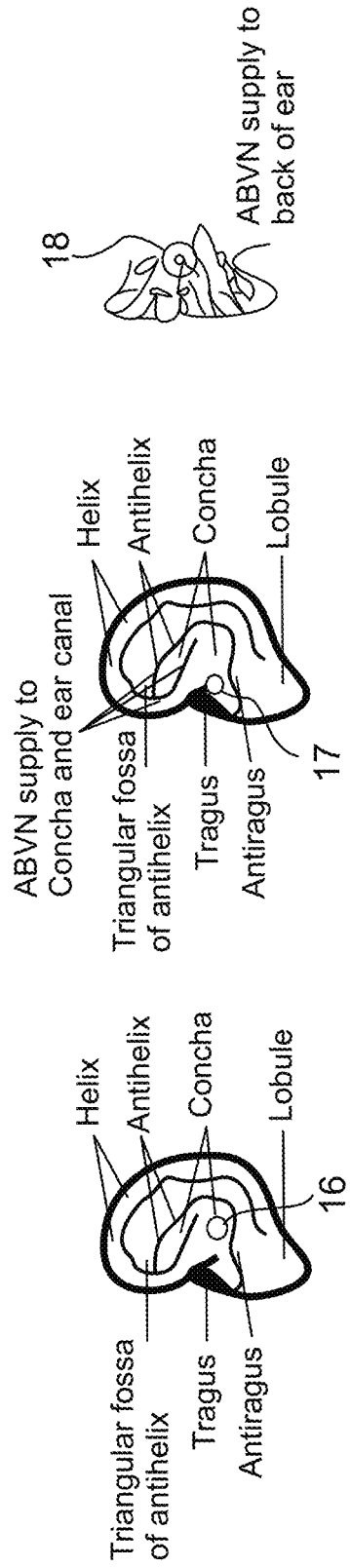
FIG. 11A
FIG. 11B
FIG. 11C
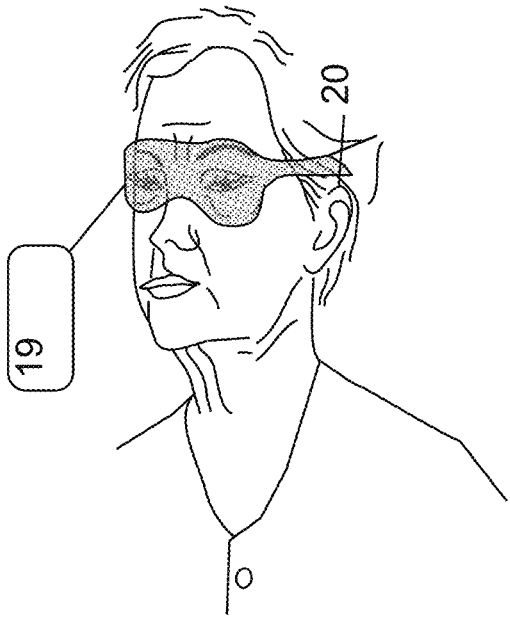
FIG. 12

SYSTEM AND METHOD FOR TREATING VARIOUS NEUROLOGICAL DISORDERS USING SYNCHRONIZED NERVE ACTIVATION

RELATED APPLICATIONS

This is a continuation of U.S. patent application Ser. No. 17/080,878 filed on Oct. 27, 2020, which is a continuation of U.S. patent application Ser. No. 16/066,335 filed on Jun. 27, 2018, now U.S. Pat. No. 10,835,735, which is a National Phase of PCT Patent Application No. PCT/IL2016/051394 having International Filing Date of Dec. 28, 2016, which claims the benefit of priority under 35 USC § 119(e) of U.S. Provisional Patent Application No. 62/271,664 filed on Dec. 28, 2015. The contents of the above applications are all incorporated by reference as if fully set forth herein in their entirety.

FIELD AND BACKGROUND OF THE INVENTION

The present invention pertains to the field of treatment of patients who suffer from neurological disorders such as, but not only, Alzheimer's, Parkinson's, tremor, depression, migraine, headache, peripheral pain, attention deficit disorder (ADD), attention deficit and hyperactivity disorder (ADHD), sleeping disorders, cognitive dysfunctions and sexual dysfunctions. More particularly, the invention pertains to treatment by activation of the nerve system using various techniques such as, but not only, electrical stimulation, sensory stimulations and cognitive stimulations. Treating neurological disorders by activating the nerve system solely, or in conjunction with medication, is commonly known but is effective only to some extent. A method for synchronized activations of the central nerve system could synergistically improve the effectiveness of the treatment and hence, could enable implementing it on therapeutic devices which are more accessible to patients and more cost effective.

The present invention also pertains to the field of providing cognitive improvement treatment using nerve stimulation, including treatment of patients who suffer from either neurological disorders such as, but not only, Amnestic Mild Cognitive Impairment (AMCI), Dementia, Alzheimer, Parkinson and Tremor, or healthy individuals who sense cognitive decline. More particularly, the invention pertains to treatment by activation of the nerve system using various techniques such as, but not only, electrical stimulation. Stimulation can be provided during sleep and may include mean to synchronize the nerve stimulus with sleep stages, like, but not limited to, rapid eye movement ((REM) sleep. In other embodiments, nerve stimulation can be delivered together with other sensory stimulation. A method for simultaneous activation of the nervous system at certain sleep stages could synergistically improve the effectiveness of the treatment and hence, could enable implementing it on therapeutic devices which are more easy to use to patients and more cost effective. Specifically, nerve stimulation may be applied, but not limited to, during REM sleep, in which intensive mental and chemical processes occur in the brain.

In one of its embodiments the present invention provides a detector which detects sleep stages. Such a detector includes but not limited to EEG sensors, eye movement sensors, and movement sensors, such as actimetry sensors, ECG analyzers, breath analyzers, and body movement trackers. The present invention includes a control unit that can activate nerve stimulation in an afferent direction, during a selected stage of sleep like REM sleep, or slow wave sleep stage (SWS). The activated nerve can be any one of the cranial nerves, including the olfactory nerve (I), the optic nerve (II), oculomotor nerve (III), trochlear nerve (IV), trigeminal nerve (V), abducens nerve (VI), facial nerve (VII), vestibulocochlear nerve (VIII), glossopharyngeal nerve (IX), vagus nerve (X), accessory nerve (XI), and hypoglossal nerve (XII). In a specific embodiment, such nerve can be the auricular branch of the vagus nerve (ABVN) with all its innervations with the greater auricular nerve, the lesser occipital nerve, and the auriculotemporal nerve.

Non-invasive access to the auricular branch of the vagus nerve is presented in some embodiments of this invention via a stimulator and one or more electrodes. These can generally be a type of stimulation device located behind the ear (BTE), in the ear (ITE), in the ear canal (IEC), or completely in the ear canal (CIC), or any combination of these.

Cognitive decline is a major concern for both the aging individual and the medical community, and in particular early malignant phenomena such as AMCI (Amnestic Mild Cognitive Impairment), which may represent the early stage of some form of Alzheimer's. The efforts to halt Alzheimer's deterioration include using drugs, mainly cholinesterase inhibitors.

An emerging medical approach is to induce neuro-modulation, using methods such as trans magnetic stimulation (TMS), transcranial direct current stimulation (tDCS), transcranial alternating current stimulation (tACS), radio electric asymmetric conveyer (REAC), transcranial electromagnetic treatment (TEMT), deep brain stimulation (DBS), vagal nerve stimulation (VNS) and its non-invasive counterpart, transcutaneous VNS (tVNS). These methods have shown positive effects with other medical conditions, such as depression, but, in general, they are at a preliminary state in determining if they possess a lasting impact on dementia progression. The invention of the present application is intended to make a contribution in using neuro-modulation to provide an impact in preventing or slowing dementia progression.

SUMMARY OF THE INVENTION

The present invention provides a system and method for treating various neurological disorders using synchronized activation of the central nervous system. In some embodiments the activation is in an afferent direction. The nerve may include one of the following nerves: the olfactory nerve (I), the optic nerve (II), oculomotor nerve (III), trochlear nerve (IV), trigeminal nerve (V), abducens nerve (VI), facial nerve (VII), vestibulocochlear nerve (VIII), glossopharyngeal nerve (IX), vagus nerve (X), accessory nerve (XI), and hypoglossal nerve (XII). For optimal cognitive effect, it is preferable to activate other body functions in parallel to nerve activation as indicated for example in FIG. 8 discussed below. The system of the invention includes various nerve activators, also sometimes denoted herein as stimulators, including direct nerve activators using electrical stimulator or cognitive activators, and indirect nerve activators such as muscle activators, or thermal activators and a control unit that controls the multiple nerve activators simultaneously. The stimulators can use various stimulation techniques, including, but not limited to, electrical stimulation, mechanical stimulation, thermal stimulation, visual stimulation and audio stimulation. The control unit uses one or more optimization methods to adjust the parameters of each activator, such as its activation timing, intensity and pattern, i.e. shape of the activation pattern.

The shape of the pattern is determined by "On" times, "Off" times, positive or negative pulses, and order of pulses. As an example of a pattern, a pattern can consist of a positive pulse at intensity I and time t follow by a negative pulse at intensity I/2 and time t*2. Each stimulation will included 10 basic pulses with 5t "off" time between each pair of basic pulses.

The present invention also provides a system and method for treating various neurological disorders using activation of the nerve system in synchrony with the different sleep stages. The system of the invention includes at least one nerve activator and a control unit that controls the at least one nerve activator in synchrony with sleep stages. The stimulator can use various stimulation techniques, including low frequency electrical current pulse stimulation, radiofrequency stimulation, mechanical stimulation, thermal stimulation, visual stimulation and audio stimulation. The control unit uses one or more optimization methods to adjust the parameters of each activator, such as the activator's activation timing, frequency and pattern.

In one aspect of the invention there is provided a neuromodulation system for treatment of physiological disorders. The system includes one or more stimulators for stimulating at least one of the cranial nerves; one or more detectors configured for detecting a predetermined physiological state; and a control unit that controls nerve stimulation by the one or more stimulators so that it is synchronized with the at least one predetermined physiological state detected by the at least one detector.

In an embodiment of the system, the physiological state is at least one sleep stage. In some cases of this embodiment one or more detectors are configured to detect one or more predetermined sleep stages selected from rapid eye movement (REM) sleep or slow wave sleep (SWS) and where the one or more stimulators provide stimulation only during the selected sleep stage. In some cases of this embodiment the one or more stimulators are configured to provide stimulation that is synchronized with a predetermined sleep stage so as to provide treatment of physiological disorders selected from a group consisting of: Alzheimer's disease, sleep disorders, other neurological disorders, and heart pathologies. The heart pathologies are chosen from heart failure and atrial fibrillation. The other neurological disorders are selected from a group of disorders consisting of: Parkinson's disease, tremor, depression, migraine, headache, peripheral pain, attention deficit disorder (ADD), attention deficit and hyperactivity disorder (ADHD), sleeping disorders, cognitive dysfunctions and sexual dysfunctions.

In some embodiments of the system, the cranial nerve stimulated is the vagus nerve. In some cases of this embodiment, the vagus nerve is the auricular branch of the vagus nerve.

In another embodiment of the system, the one or more stimulators are non-invasive stimulators positioned at a location selected from the group of locations consisting of: behind the ear (BTE) of a patient, in the ear (ITE) of a patient, in the ear canal (IEC) of a patient, and completely in the ear canal (CIC) of a patient.

In other embodiments of the system, the control unit is configured to provide a feedback mechanism that controls one or more stimulators. In some cases of this embodiment, the feedback mechanism is selected from a group consisting of the following mechanisms: feedback mechanism based on the patient's heart rate; feedback based on a cognitive test result; feedback mechanism based on sleep stage; and feedback based on an EEG parameter.

In yet another embodiment of the system, the system includes a wired connection between the one or more detectors, the control unit, a power supply and the one or more stimulators.

In still another embodiment of the system, the system includes a wireless connection to a remote control unit.

In yet other embodiments of the system, the one or more stimulators are at least two stimulators.

In another embodiment of the system, the one or more stimulators are two or more stimulators each different from the other simulators; each providing a different type of stimulation.

In another aspect of the present invention there is provided a method of neuromodulating a patient for treatment of physiological disorders. The method includes the steps of: detecting a predetermined physiological state; and applying stimulation to one of the cranial nerves during the predetermined physiological state by one or more stimulators of a neuromodulation system.

In an embodiment of the method, the cranial nerve is the vagus nerve. In some cases of this embodiment, the cranial nerve is the auricular branch of the vagus nerve (ABVN).

In another embodiment of the method, the method further includes a step of placing one or more stimulators of the neuromodulation system as described above into a patient's ear for stimulation of the ABVN.

In another embodiment of the method, the physiological state is a specific sleep stage. In some cases of the embodiment, the specific sleep stage is selected from a rapid eye movement (REM) sleep stage or a slow wave sleep (SWS) stage.

In yet another embodiment of the method, the neuromodulation is delivered for treatment of Alzheimer's disease.

In a further embodiment of the method, the method further includes a step of optimizing the one or more stimulators to provide stimulation for treatment of physiological disorders selected from a group consisting of: Alzheimer's disease, sleep disorders, other neurological disorders, and heart pathologies.

In still another embodiment of the method, the step of applying one or more stimulators is the step of applying two or more stimulators. In yet another embodiment, the two or more stimulators are different stimulators providing different types of stimulation.

Terminology

"Stimulation" and "activation" and words derivative therefrom are used synonymously herein unless specifically indicated otherwise. For example "activate" is synonymous with "stimulate" and "activator" is synonymous with "stimulator". "Stimulator" when used herein contains all elements necessary for stimulation including elements such as the stimulator electrodes unless these elements is discussed separately in the text.

"Sensor" and "detector" and words derivative therefrom are used synonymously herein unless specifically indicated otherwise. For example "sense" is synonymous with "detect" and "sensing" is synonymous with "detecting".

"Pattern" or "stimulation pattern" has been used herein to mean pulse shape (intensity, duration, polarity, tooth shape or square shape etc.), rest times between pulses and modulation thereof (each pulse duration is 10% more than previous one, up to 200% and then decreasing by 10% until 100%), for example intermittent activation or periodically changing of one of the stimulation intensities.

"Optimization" in the context of this application means setting of stimulation parameters like frequency or intensity of each stimulator to receive the strongest response while keeping away from inducing pain to the patient. If more than one stimulator is used, optimization will mean in addition, finding the best combination of synchronization in time and intensities to activate the stimulators to provide the strongest response as detected by the relevant detector, "Optimization methods" in this respect will mean the algorithm to find the optimal activation parameters, like scanning through each activation parameter while holding the rest fixed, or more efficient algorithms that reduces the scan time, for example starting from the strongest stimulation and reducing to bearable pain.

BRIEF DESCRIPTION OF THE SEVERAL VIEWS OF THE DRAWINGS

The disclosed inventions will be described with reference to the accompanying drawings, which show important sample embodiments of the invention and which are incorporated in the specification hereof by reference, wherein:

FIGS. 11A to 11C show various options for positioning an electrode of a stimulator in the ear;

FIG. 12 is a schematic illustration of a fourth embodiment of the proposed system;

DETAILED DESCRIPTION OF THE INVENTION

Figure 1:
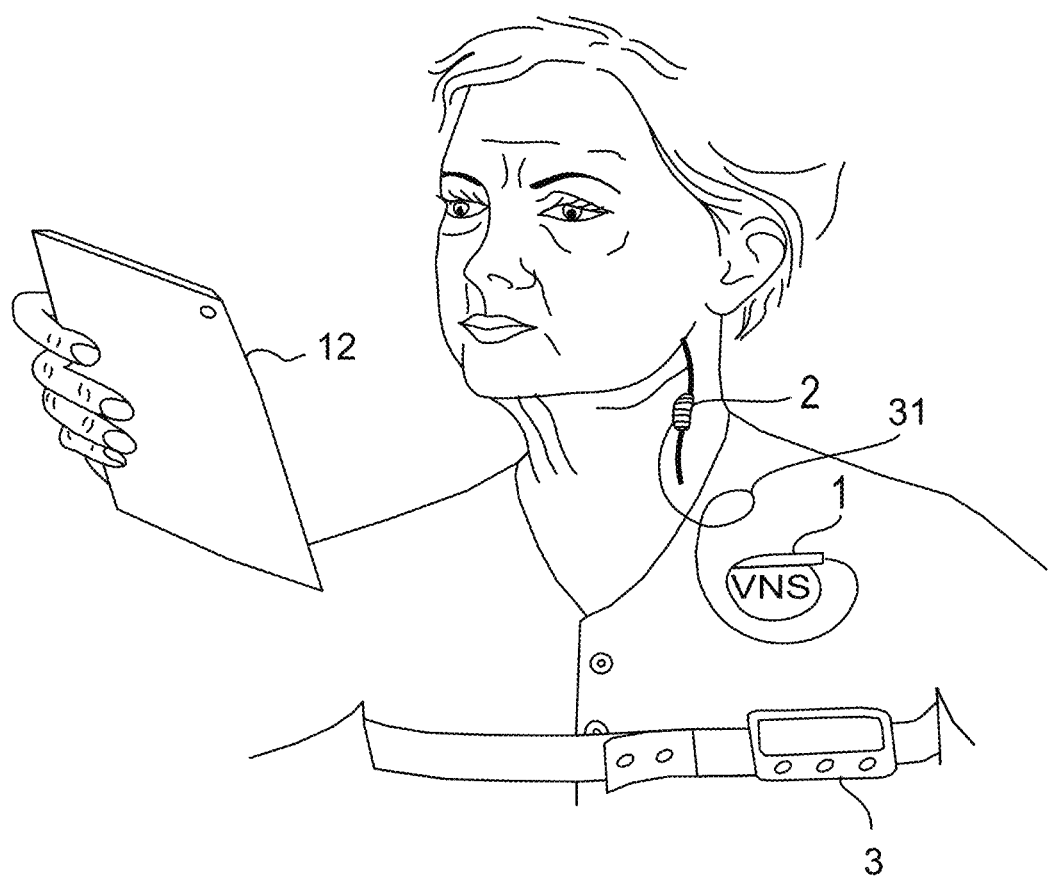
FIG. 1 is a schematic illustration of one embodiment of a proposed implanted stimulation system.

The present invention introduces an effective way to deliver one or more neurological activations for the treatment of neurological disorders. Nerve activators using different activation techniques may be controlled by a single control unit.

Activators that may be used can provide at least one of the following types of stimulation:

Electrical stimulation may be provided by a wide spectrum of activators, including sensory nerve activators and/or muscle activators. A specific example for this invention is stimulation of the vagus nerve. In a specific embodiment, such activation is done in an afferent direction, resulting in activation of brain centers that are linked to the vagus nerve. The stimulation can be effected by using an implanted nerve stimulator and a stimulation lead. Electrical nerve stimulation can also be effected by stimulation of nerves using a non-invasive external electrical stimulator. Electrical stimulation of muscle can be effected by activation of limb muscles at a predetermined frequency and intensity. (See FIG. 2 and description thereof herein below.) A specific electrical activation embodiment includes activation of the human foot. Such activation can trigger both nerve stimulation and muscle stimulation. Another embodiment of electrical activation is to activate the body at known locations that are used for acupuncture treatment. Another nerve stimulation technique which may be used is an external nerve stimulation technique known as transcutaneous electrical nerve stimulation (TENS). (See FIG. 3 and description thereof herein below.) A specific example of such TENS configuration is stimulation of the auricular branch of the vagus nerve (ABVN) that is located in the ear of the subject.

Mechanical stimulation may be provided by a wide range of techniques, including pressure stimulation and vibration stimulation. In a specific embodiment, mechanical stimulation includes a vibrator that mechanically activates the human carotid nerve in the neck (see FIG. 6 and description thereof herein below) which in turn activates the vagus nerve. Another specific embodiment includes mechanical activation of a human foot. (See FIG. 4 and description thereof herein below.) Such activation can be done in specific spots that are normally used in Shiatsu therapy.

Thermal stimulation can be used either for full body activation, or selected spot activation. Full body activation can include placing the patient in a controlled temperature environment or a hot tub. Alternatively, such thermal activation can be applied to a specific spot on the patient's body. In a specific embodiment, such activation can be applied to the patient's foot. (See FIG. 5 and description thereof herein below.) In another embodiment, the thermally treated spot can be the head of the patient.

Visual stimulation can be effected by presenting light patterns to the subject. Such light patterns can be alternating light with a predetermined frequency. It can include known images, for example, or a sequence of images. In a specific embodiment such sequence may include images of faces, which may include known faces or a mixture of known and unknown faces.

Audio stimulation can be effected by presenting an audio pattern to the subject. Such audio pattern may include specific sounds, both known and unknown. It can include alternating sounds that are presented at a predetermined frequency. In a specific embodiment, such audio activation may include playing a musical piece that is familiar to the subject.

Cognitive stimulation is targeting the activation of the brain to perform cognitive activity such as reading, mathematical calculation, logic challenges, emotional reaction such as happiness, and sadness. In a specific embodiment, such activation may include a questionnaire that the subject should complete. Another embodiment may include an emotional visual that can trigger an emotional state in the subject. Cognitive activation can use tools like an interactive tablet computer (see FIG. 1 and description thereof herein below) with a dedicated application that generates cognitive stimulation and collects responses from the patient.

The control unit of the system can include several communication links to interact with the one or more activators. Specific examples can be magnetic activation of an implantable nerve stimulator and remote activation of a computer-based cognitive stimulator. Another example of specific activation can be simultaneous activation of two or more separate implantable devices. These may be similar devices or different devices.

Additionally, in some embodiments, the control unit can be configured to include power source to power the various activators wirelessly. A specific example of wireless powering can be using inductive coupling as an implantable nerve stimulator.

The control unit can be designed to be an external, portable, easy to carry device that can be attached to the patient's body using a wearable element. (See FIG. 7 and description thereof herein below.)

Another embodiment of the control unit can include two separate parts: one part that is wearable and contains all the communication links and a second part that implements the user interface and the algorithms for optimization methods.

Figure 8:
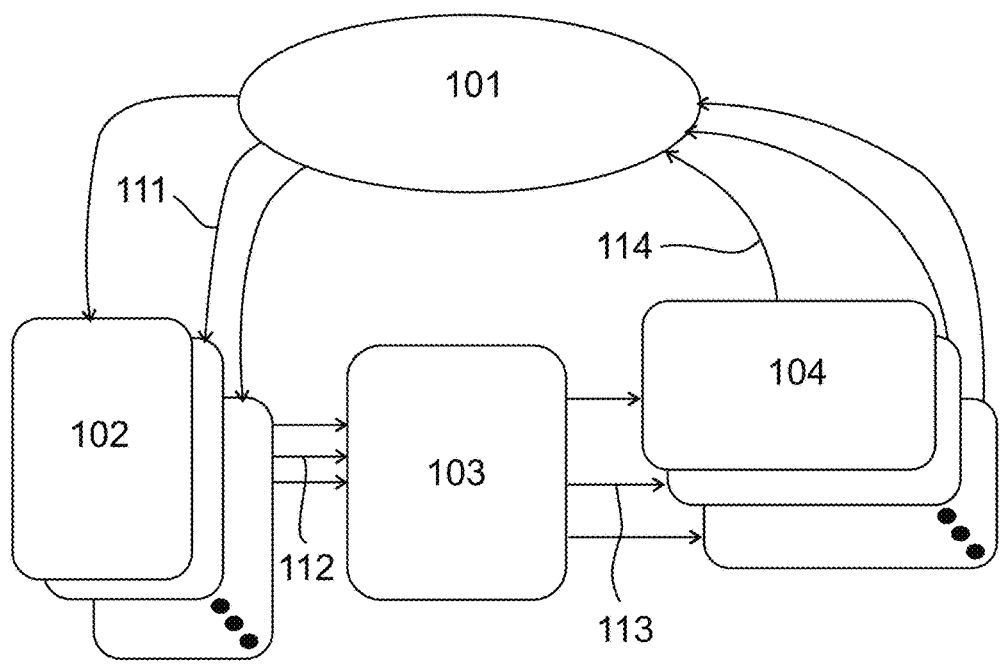
FIG. 8 illustrates a block diagram depicting stimulation based on optimization methods

The control unit can use several control algorithms to enhance or optimize the stimulation effectiveness as described in FIG. 8, including:

Adaptively based on cognitive response—Stimulation during specific sleep stages like REM sleep;

Inducing specific cognitive state, sadness for example, for best stimulation effectiveness;

A feedback mechanism in which stimulation is imposed in response to specific phenomena detected by the detector;

Close loop adjustments of the stimulation intensity or frequency in real time in response to detection of cognitive or physiological parameters;

Combined synchronize stimulations from more than one stimulator to elevate the cognitive effect;

Pin point the most effective stimulation timing by combining reading from more than one detector to find the most effective timing for stimulation;

Adaptively based on EEG patterns, for example, the intensity of theta waves or other EEG patterns that indicate different sleep stages;

Adaptively based on a subject's physical activity intensity, for example during rest or exercise periods;

Adaptively based on heart rate (HR), for example, during HR elevation or when the HR is above a set threshold.

An external or internal sleep sensor provides input on the sleep stages. The sleep sensor unit can include several communication links to interact with an activator. A specific example can be a magnetic activator for providing magnetic activation of an implantable nerve stimulator.

Another specific activation can be using Bluetooth signaling to a non-invasive tVNS ABVN stimulator.

A specific example of a sleep sensor is an 'under the mattress' sleep sensor, using an electro-mechanical sensor, such as a piezo-electric sensor. (See FIG. 16 and description thereof herein below). The sensor may be connected wirelessly to an implantable stimulator. The electrode of the stimulator is located in the subject's neck and intended to stimulate the vagus nerve (see FIG. 9 and description thereof herein below), or to a non-invasive tVNS stimulator with an electrode attached to the external ear. (See FIG. 12 and description thereof herein below.) The tVNS circuitry can be located behind the ear, in the ear, or in the ear canal. The stimulator can be self-powered, or wirelessly in communication with an energy source, or in a wired connection with an energy source.

The tVNS electrodes can be attached to the concha, to the ear canal surface, or have its electrodes split between the concha/external auditory canal, and the back of the ear, or both electrodes at the back of the ear. (See FIGS. 11A, 11B and 11C and 18 and descriptions thereof herein below.)

It is to be understood that the embodiments of the electrode herein described are merely illustrative of the application of the principles of the invention. It will be appreciated that many variations, modifications, among them ones based on ergonomic considerations, to allow comfortable use of the device during sleep, may be made. The ear Bluetooth unit can have its antenna on a chip, or to be printed or embedded in soft encapsulation.

The stimulation electrode attached to skin near the ABVN can provide surface current pulses through monopolar electrodes, in the form of surface current, or through the ear tissue, where one monopolar electrode is located at the back of the ear at one of ABVN locations, and the other monopolar electrode is at the concha, or in the external auditory canal.

In some configurations, stimulation can be applied through both locations simultaneously using several monopolar electrodes placed in the concha, in the external auditory canal or in other places inside the ear canal, using a reference electrode placed at the back of the ear.

A sleep sensor may be of an eye mask type, a movement sensor or an electrical signal sensor that can be integrated into the ear stimulator. The sleep sensor may be connected to the ear stimulator via wires or via wireless communication, such as via a Bluetooth connection. (See FIG. 13 and description thereof herein below.)

The sleep sensor can use EEG signals measured from the head using dedicated electrodes. The EEG electrodes can be used for detecting sleep stages and changes in hippocampus activity, for example by monitoring theta waves.

The device may have all its elements: power source, sleep sensor, control unit, stimulator in a single unit, or have all elements in one unit except for one of the following: the sleep sensor, the control unit, or the stimulation electrodes.

In some cases, the stimulator can be placed simultaneously in both ears. (See FIG. 20 and description thereof herein below.) In such a case, stimulation can be done simultaneously, or separately. The system may include a heart rate (HR) monitor that may enable closed loop evaluation with any of the stimulation parameters, including time of activation, frequency and intensity. In a specific embodiment, if the HR monitor detects reduction in heart rate by more than a preset value due to stimulation it stops or reduces the stimulation intensity until the effect of activation is reduced below the preset value. Such preset value can be any value between 1 beat per minutes (BPM) and 10 BPM.

Optimization can mean in one embodiment (see FIG. 1 and description thereof herein below) reacting to the patient input as sensed through the answers the patient gives to the tablet questionnaire. When the patient is in a specific cognitive state, sadness for example, the stimulation will be activated.

Cognitive stimulation using tVNS excitation (see FIGS. 10 and 14 and description thereof herein below) or other cranial nerve stimulation can be synchronized to perform stimulation at the same time that the brain performs cognitive activity such as reading, mathematical calculation, logic challenges, and/or undergoes emotional reactions such as happiness, and sadness.

In a specific embodiment such activation may include a questionnaire that the subject should answer. Another embodiment may include showing an emotion inducing picture that can trigger an emotional state in the subject. The cognitive activation can use tools such as an interactive tablet computer with a dedicated application that generates cognitive stimulation and collects responses from the patient. (See FIG. 1 and description thereof herein below.)

Sensory stimulation such as music can be added simultaneously with tVNS activation or other cranial nerve stimulation. Such activation can be initiated during specific sleep stages. In a specific embodiment, such audio activation may be by playing music that is familiar to the subject.

Additionally, in some embodiments, the control unit can include a power source for powering the stimulator to which it is in wireless connection. A specific example can be powering the activator wirelessly by using inductive coupling.

The tVNS stimulation or other cranial nerve stimulation may be used for improving the quality of sleep. Specifically, this can be affected by inducing additional periods of REM sleep or by prolonging the REM sleep periods when they occur.

Sensory stimulation such as music or smell can be added simultaneously using tVNS activation while the user is awake.

The control unit can use one or more of the following optimization methods to adjust the stimulation's timing/synchronization, intensity and patterns. (See FIG. 8 and description thereof herein below.):
  Adaptively based on cognitive response potency
  Stimulation during REM sleep periods or during other types of sleep stages such as slow wave sleep (SWS)
  Adaptively based on EEG patterns
  Adaptively based on physical activity intensity
  Adaptively based on heart rate The tVNS stimulation unit can be made of soft materials which enables it to be inserted into an ear with minimal effect on the subject's sleep. The tVNS stimulation unit can be a type of device located behind the ear (BTE), in the ear (ITE), in ear canal (IEC), or completely in ear canal (CIC), as in FIGS. 11A, 11B, and 11C and FIG. 18 (see descriptions thereof herein below), or any combination of these. It may include more than one stimulation electrode. The device may include a control unit that can select the most efficient electrode set based on stimulation parameters for each specific sleep stage.

The CIC type device can be made of three units (see FIG. 15 and description thereof herein below), the stimulating section with its electrodes, wireless connection section and a battery. The device may have an arm, to assist insertion and removal of the device from the ear canal. The ear neuromodulation platform has an internal structure, with elastic spacers between its components. It may have a form or arrangement of its components, e.g. of the battery, stimulator and wireless communication, and its encapsulation that allows it to conform with, or be adjustable to, the ear anatomy, in particular to the varying anatomical cross-section of the ear canal. (See FIG. 19 and description thereof herein below.).

The ear unit has a means to adjust the properties of the stimulation waveform, such as the amplitude of the pulses, via programming of the control unit. The control unit can be accessed for parameter setting, with no contact to stimulator's circuitry or using a port for programming or having embedded potentiometers with access to adjusting tool such as screwdriver.

Control of activation parameters can be affected using remote control from an external device. The activation parameters, such as electrical current pulse amplitude, can be re-adjusted based on the patient's feedback and also by using a cognitive test to evaluate the cognition potency. Alternatively, it can be readjusted based on the sleep parameters such as the duration of the REM sleep stage.

Figure 16:
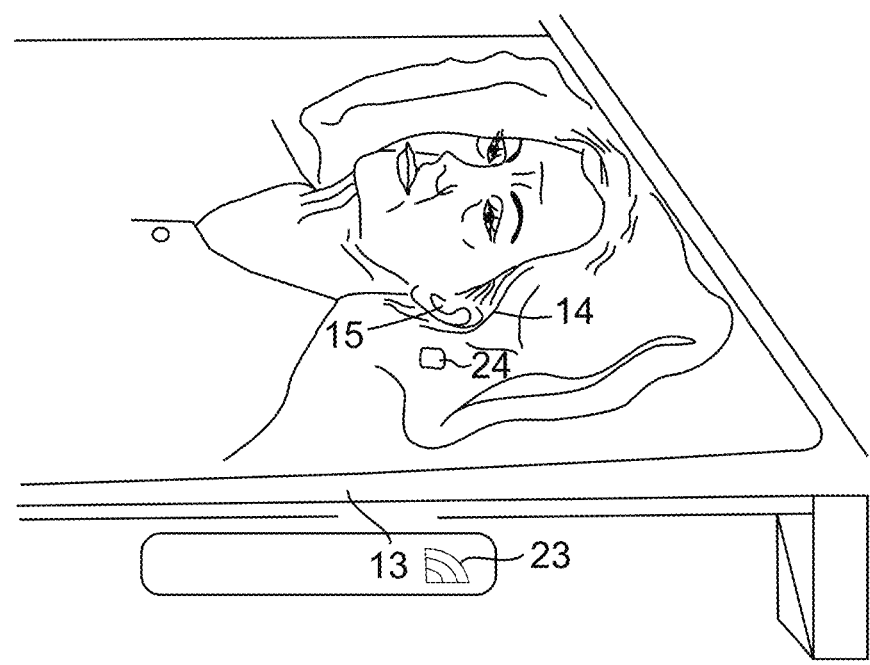
FIG. 16 is a schematic illustration of a seventh embodiment of the proposed system.

An embodiment of the proposed system is comprised of electrical activation by the tVNS platform using a non-invasive stimulator and a sensor under or in a sleep mattress, with a Bluetooth communication link incorporated into both, as shown in FIG. 16. (See description thereof herein below). Its schematic operation is diagramed in FIG. 17 (see description thereof herein below).

Figure 15:
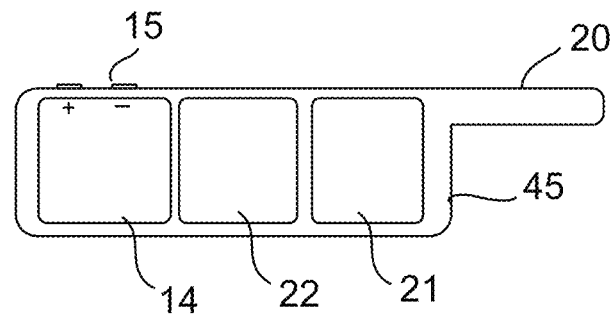
FIG. 15 is a specific implementation of a tVNS device for positioning completely in ear canal (CIC).
Figure 19:
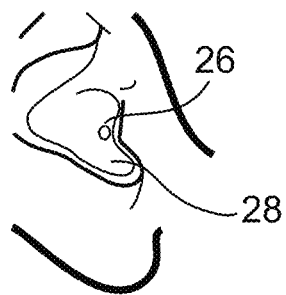
FIG. 19 depicts an in-the-ear stimulation device.

All device types, including BTE, ITE as seen in FIGS. 11A, 11B and 11C, or standalone CIC type shown in FIGS. 15 and 19, may have_a hole in the middle for minimal sound blockage and equalized air pressures.

The stimulation electrodes can be made of metal contacts shaped to optimally provide the electrical or heat pulses. They can be made of, or coated with, conductive adhesive material or conductive fabric.

There can be electrodes placed in both ears (see FIG. 20 and description thereof herein below.), where the electrodes can be used for sensing and stimulation. The electrodes can be connected wirelessly or by wires and can measure the electrical potential difference between the two ears. In such a case, the configuration may include a band that is placed at the back of the neck and at the forehead, or only at the back of the neck, or over the head or with a hat net.

The simulation can be applied in conjunction with or in relation to drug administration, in such way that the stimulation is synchronized with drug intake, or during the time when it is active. Nerve stimulation can enhance or suppress release of chemicals by the brain, such as neurotransmitters, in a timely manner with regard to drug activity.

An embodiment of this invention includes a neuromodulation platform for treatment of neurological disorders comprising: a sensor measuring the parameters of specific body action; at least one nerve activator; and a control unit synchronizing the nerve activator to the body actions.

The nerve activator can be one of the following stimulators:
  Electrical stimulator
  Mechanical stimulator
  Thermal stimulator
  Visual stimulator
  Audio stimulator
  Cognitive stimulator In a specific embodiment, the neuromodulation includes at least three activators.

In some embodiments, the electrical stimulation is stimulation of the vagus nerve using an implantable stimulator.

In some embodiments, the control unit of the stimulator includes a non-implantable magnetic wand that communicates with the implantable vagus nerve stimulator.

The apparatus described above may also include a second stimulator that provides cognitive stimulation. The cognitive stimulator described above may also comprise a computerized viewer that is controlled by the control unit.

In some embodiments, the nerve activator can be implemented in one of the following platforms:
  A completely implantable device
  A device including an external control unit and an implantable activator
  A device that is in direct contact with the treated subject's skin
  A device with a control unit that is not in contact with the subject being treated and an activator that is in direct contact with the treated subject skin
  A device that is totally not in direct contact with the treated subject In some embodiments, the control unit for treatment of neurological disorders includes:
  A processing unit; and
  At least one communication module, each module in communication with a separate nerve activator.

The communication modules described above may perform communication through one of the following techniques:
  Magnetic field transmission
  Electrical field transmission
  Optical transmission
  Wireless transmission
  Wire electrical transmission
  Electrical stimulation
  Mechanical stimulation
  Thermal stimulation
  Visual stimulation
  Audio stimulation
  Cognitive stimulation The control unit described above may include a cognitive sensor for sensing cognitive markers or physiological signals.

The control unit described above may include an adaptive control mechanism that can change the parameters of the activator based on an input from the cognitive sensor.

The control unit described above may include an eye tracking sensor that detects the onset of rapid eye movement periods during sleep.

The control unit described above may include a cognitive sensor that detects the intensity of cognitive activity and synchronizes the activator to apply stimulation during a period of high cognitive activity.

In some embodiments, the processor that is connected to a control unit that is used for treatment of neurological disorders includes a data recording means that records at least one of the following inputs:
  The parameters of the activator
  The cognitive intensity as measured by EEG sensors or cognitive questionnaire
  Physiological signals such as heart rate, onset and termination of REM sleep periods, EEG, activity sensor, body temperature and bio-impedance The processor of the control unit described above may include an analyzer to perform multi-parameter analysis of the patient condition during treatment and during time between treatments.

The current invention also relates to a neuromodulation platform for treatment of neurological disorders comprising: at least two parallel brain activators as shown in FIG. 8. and a control unit that controls the activation parameters and synchronizes the multiple activation processes In some embodiments, the brain activation processes involves one of the following types of cognitive stimulations: audio, cognitive challenge, such as reading, solving puzzles, logic tasks and emotional challenge, such as experiencing happiness, fear or an excitement.

In some embodiments, the neuromodulation platform comprises a vagus nerve stimulator and a detector for detecting sleep stages In some embodiments, the neuromodulation platform is configured to detect REM sleep and provide stimulation only during REM sleep periods In some embodiments the neuromodulation platform includes an ear stimulation platform to stimulate the auricular branch of the vagus nerve (ABVN).

In some embodiments, the neuromodulation platform is configured to affect concentrations of bio-chemicals in the brain, such as proteins and neurotransmitters.

In some embodiments, the neuromodulation platform is configured to provide stimulation that is synchronized with sleep stages and to treat physiological disorders such as Alzheimer's, sleep disorders, neurological disorders and heart pathologies such as heart failure and atrial fibrillation In some embodiments, the ear stimulation platform comprising a non-invasive nerve activator includes one of the following configurations: an activator located behind the ear (BTE); an activator located in the ear (ITE); an activator located in the ear canal (IEC); and an activator located completely in the ear canal (CIC).

In some embodiments, the ear stimulator comprises at least one set of radial anode and cathode electrodes placed at the ear canal.

In some embodiments, the ear stimulation platform comprises an ear canal part with a middle core that enables sound transmission.

In some embodiments, the middle core can be an open void.

In some embodiments, the ear stimulator comprises an internal structure and encapsulation that allows it to conform to, or be adjustable with, the ear anatomy In some embodiments, the ear stimulator includes a sound generator.

In some embodiments, the neuromodulation platform includes two ear stimulators, one placed in the right ear and one in the left ear (See FIG. 2 and description thereof herein below)

In some embodiments, the neuromodulation platform comprising two ear stimulators one for each ear, that have a connecting wire. In some embodiments, the neuromodulation platform comprises a feedback mechanism that controls the stimulation.

In some embodiments, the feedback mechanism is selected from one of the following mechanisms: feedback mechanism based on heart rate; feedback mechanism based on EEG parameters measured by EEG electrodes; and feedback mechanism based on cognitive test results.

In some embodiments, the neuromodulation platform comprises an electrical signal sensor and an ear stimulator.

In some embodiments, the neuromodulation platform comprises a stimulator for stimulating the auricular branch of the vagus nerve and further comprising at least one anode and at least one cathode electrode that are in direct contact with the skin of an ear of the subject.

In some embodiments the neuromodulation platform comprising at least one electrode placed in one of the following locations selected from the group of locations consisting of: the back of the ear, the concha and the ear canal.

In some embodiments the neuromodulation platform comprises a sleep sensor in electrical communication with a processing unit and a communication module. The sleep sensor may detect at least one of the following parameters: onset of rapid eye movement during sleep, EEG signal, body activity, and heart rate.

In some embodiments, the neuromodulation platform may have a control unit that adjusts the amplitude of the stimulation pulses, using an adjustable potentiometer.

In some embodiments, the neuromodulation platform is a platform for promoting drug administration having a stimulator for stimulating the auricular branch of the vagus nerve. The platform comprising: an ear canal stimulation electrode of the stimulator; a drug delivery system for delivering a drug; and a control unit for synchronizing nerve stimulation with the timing of drug administration.

In some embodiments, the drug delivery system is adapted for delivering insulin.

In some embodiments, the drug delivery system is adapted for delivering drugs that are targeting the central nervous system In some embodiments, the drug delivery system is adapted for delivering drugs for treatment of cardiac pathologies In some embodiments, the drug delivery system is adapted for delivering drugs for treatment of cancer In an embodiment, a neuromodulation platform for treating ADD or ADHD, the platform comprises:
  an EEG detector for measuring an EEG signal;
  a control unit establishing ADHD functional status using an analysis of the EEG signal;
  a stimulator for stimulation of the auricular branch of the vagus nerve of the subject; and
  a control unit that adjusts the stimulation parameters of the stimulator based on the established ADHD functional status.

In an embodiment, a neuromodulation platform for treating depression, the platform comprising:
  an EEG detector for measuring an EEG signal;
  a detector for determining a depression status using EEG signal analysis;
  a stimulator of the auricular branch of the vagus nerve of the subject; and
  a control unit that adjusts the stimulation parameters for the stimulator based on the determined depression status.

It should be noted that there is a standard depression status ladder and depression level is assessed accordingly.

In an embodiment, a neuromodulation platform for treating migraines, the platform comprising:
  an EEG detector for measuring an EEG signal;
  a controller for determining a migraine status using an analysis of the EEG signal;
  a stimulator for stimulation of the auricular branch of the vagus nerve of the subject; and;
  a control unit that adjusts the stimulation parameters of the stimulator based on the detected migraine status.

Electrical stimulators when electrical stimulation is used may be selected from among the following:
  Current control stimulator
  Voltage control stimulator
  Charge control stimulator
  Monophasic stimulator
  Dual phase stimulator
  Multiphase stimulator
  Single polarity stimulator
  Dual polarity stimulator The above list is not intended to be an exhaustive list.

The stimulators or detectors listed above may use different electrodes to deliver the stimulation or sense physiological parameters like EEG or ECG, such as:
  Capacitance electrode (nonconductive) for optimal biological interface assuring no electrons pass to the biological ion-charge system
  Conductive electrode enabling delivery of larger charges in specific time intervals
  Hybrid electrode, mostly capacitance with a residual of conduction, may be used as a compromise between the two prior types
  Mono-polar electrode can be used for better charge delivery, that is maximum usage of electrode area to deliver the same polarity
  Bi-polar electrode to enable better stimulation localization
  Reference electrode serving as grounding for most stimulation devices
  Dual-use electrode, for both sensing and stimulation. This requires high capacitance and high isolation between the sensing and stimulation functions
  Implantable nerve electrode will be warping the target nerve to increase the contact area and ensure good contact for long time periods.
  Wet electrode refers to an electrode with conductive hydrogel placed on top of it to improve conduction (decrease the resistance) between the electrode and the subject's skin or other organ.
  Dry electrode refers to an electrode that has a good skin interface and doesn't require a conductive hydrogel.

It should be apparent to persons skilled in the art that the stimulator electrodes used may be different from the sensing electrode used by detectors, also sometimes denoted herein as sensors, like EEG or ECG.

Detectors usable in the systems described herein may include the following:
  EEG sensors containing at least two electrodes up to as many as 16 electrodes. These sensing electrodes can be dry or wet type electrodes.
  ECG sensor or heart rate sensor to sense heart rate and other heart events like tachycardia or other heart conditions. This sensor may be implemented by a photoplethysmography (PPG) sensor, or surface ECG sensor or implantable ECG sensor.
  Sleep sensor to monitor and differentiate sleep stages like REM or SWS. Sleep sensor may include 'under the mattress sensor', wearable sensor like watch type or remote sensor like desktop sensor. The sleep sensor may be based on technology like electro-mechanical sensor, such as a piezo-electric sensor, or a micro electro-mechanical system (MEMS) accelerometer.
  Motion sensor or actimetry sensor to monitor the activity intensity of the patient, like laying, seating, standing, walking etc.
  Breathing sensor to monitor the subject's breathing function.
  Eye tracking sensor may be used to distinguish sleep conditions like REM sleep or awake conditions like reading Cognitive stimulators may include: computer base stimulator like tablet, desktop, television, or smartphone. These devices may or may not interact with the patient. They may stimulate visual, audio and other senses in two dimension or three. These devices may implement virtual reality or augmented reality to stimulate the patient. Cognitive stimulation may require the patient to preform one or more of the following activities: reading, watching, answering a questionnaire, listening, orientating in 2-dimensional or 3-dimensional space. Specific stimulation can focus on different brain activities like mathematical problems, memory challenges, verbal tasks, visual tests, gross motoric functions or fine motoric functions, and more.

Mechanical stimulators apply local pressure in different frequencies. Low frequency (up to 2 Hz) will feel like a pressure wave to the patient, and medium frequency (2 to 30 Hz) will feel more like vibrations. High frequencies (more than 30 Hz) are hard to feel directly but still may have nerve stimulation effects. The mechanical stimulator will require a mediator, like muscle, limb, or artery to stimulate an adjacent nerve and evoke a brain response. For example, massage (low frequency pressure wave) of the carotid artery is known to affect the carotid branch of the vagus nerve and induce unconscious.

Thermal stimulators apply local heat or cold at specific spots on the body or to a whole organ. The stimulation effect, mediated by biological tissue like skin or tooth, to the nervous system conveys the sensed heat or cold to the brain. Thermal stimulation like feeling cold may heighten the patient's sensing, improving other stimulation effects, for example cognitive or electrical effects when the two stimulations are applied in time synchronization.

Audio stimulators carry sound to a patient's ear through the air or by direct bone conduction. Audio stimulation is known to induce mode changes in a patient which in turn may enhance a patient's sensitivity to cognitive or electrical stimulation.

A therapeutic method is describe herein intended to treat a physiological disorder from the list of: Alzheimer's Parkinson's, tremor, depression, migraine, headaches, peripheral pain, attention deficit disorder (ADD), attention deficit and hyperactivity disorder (ADHD), sleeping disorders, cognitive dysfunctions, arterial defibrillation and sexual dysfunctions.

The method consists of stimulating cranial nerves, often, but without intending to limit the invention, the vagus nerve at specific physiological states to elicit a best therapeutic effect. Some physiological states comprise relevant events for therapy in each of the above disorders, for example, elevated cognitive state enhances vagus nerve stimulation (VNS) effect on cognition. Accordingly, by detecting the specific elevated cognitive states and applying VNS at this specific time, cognition rehabilitation may occur. An elevated cognition state can occur while the patient is sleeping (REM sleep) or while awake (in an intense cognitive challenge state).

The method may control the stimulation based on reading of physiological state detectors, like a motion detector, a brain activity detector such as an electroencephalograph (EEG) detector, a heart rate detector such as electrocardiogram (ECG) and others. The method may adjust stimulation to occur at specific times based on the physiological detectors thereby producing the best cognitive effect. Furthermore, the method may adjust in real time the stimulation intensity or frequency to reflect the physiological detector reading representing the patient's physiological state.

A special physiological state of therapeutic interest is sleep where the therapy can be administered to the patient with minimal discomfort. During sleep several distinguishable cognitive states like REM sleep or slow wave sleep (SWS) affect specific brain areas. A method administrating stimulation in conjunction with these states may result in cognitive rehabilitation. The described method can use non-invasive VNS or transcutaneous VNS (tVNS) simplify therapy administration and allow its use for the general population. More specifically, it allows for treatment of patients in moderate condition (which preclude them from invasive solutions) or those which cannot undergo invasive surgery. tVNS can be applied to two main locations, the carotid branch and the auricular branch of the vagus nerve. The auricular branch (ABVN) is better suited for prolong administration of therapeutic device described in this method.

DETAILED DESCRIPTION OF FIGURES

The following description should be read in conjunction with the Description of the Invention that appears above.

The numerous innovative teachings of the present application will be described with particular reference to presently preferred embodiments (by way of example, and not of limitation). The present application describes several inventions, and none of the statements below should be taken as limiting the claims generally. Where block diagrams have been used to illustrate the invention, it should be recognized that the physical location where described functions are performed are not necessarily represented by the blocks. Part of a function may be performed in one location while another part of the same function is performed at a distinct location. Multiple functions may be performed at the same location.

FIG. 1 depicts a schematic illustration of one embodiment of the proposed system which comprised of electrical activation by VNS using implantable stimulator (1), an interactive tablet computer (12) for cognitive stimulation, and a wearable control unit (3). A patient implanted vagus nerve stimulation system (1) including vagus nerve electrode (2) which is attached to the vagus nerve. The vagus nerve electrode (2) is connected to the nerve stimulator (1) by a flexible lead (31). An external wearable control unit (3) is worn as a necklace on the neck and placed close to the nerve stimulator (1) to enable communication between the control unit and the nerve stimulator. The control unit (3) can be placed in proximity of the implantable stimulator using a vest, a belt or a sticker. The control unit which can control wirelessly one or more activation means as illustrated in the other figures synchronizes the VNS stimulation with the other stimulation mean(s) and synchronize timing and intensities of the VNS stimulation to the other stimulation mean(s) parameters.

Figure 2:
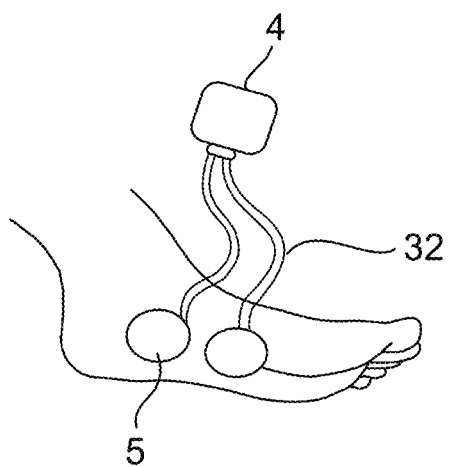
FIG. 2 is a schematic illustration of an example of electrical stimulation of a patient's foot.

FIG. 2 illustrates a specific embodiment of an external electrical stimulation system to the foot of a patient. Electrodes (5) are attached to the foot of the patient and connected to stimulation generator (4) via connecting wires (32). The electrodes may be disposable or reusable and may be self-adhesive or otherwise attached to the foot. Additionally, the electrode may be implemented in footwear and accessories to footwear such as shoes, socks and stockings. The stimulation generator is connected wirelessly or via wires to a control unit (not shown in this Figure) and may be internally or externally powered.

Figure 3:
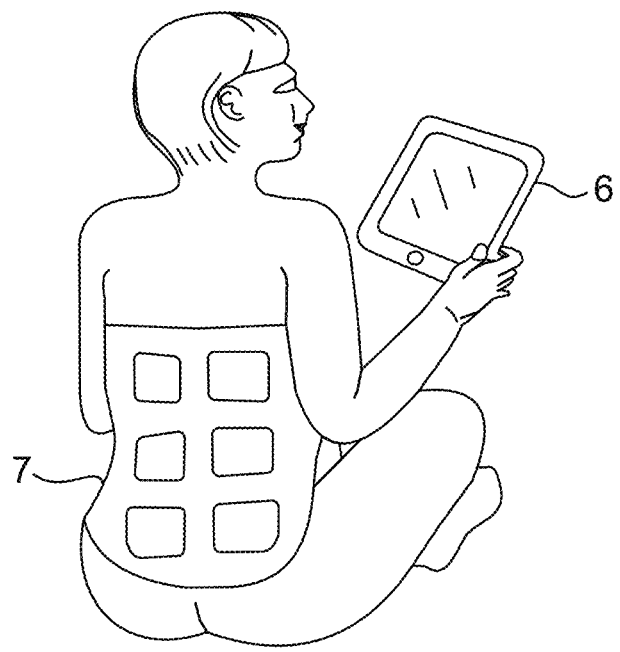
FIG. 3 is a schematic illustration of an example of electrical stimulation of a patient's back.

FIG. 3 illustrates another embodiment of external electrical stimulation using TENS (Transcutaneous Electrical Nerve Stimulation). A TENS unit (7) that comprise of electrodes and a stimulation generator is attached to the patient back. The TENS unit is controlled wirelessly or via connection wires by a control unit (not shown in this Figures). In the instant embodiment, another stimulator, an interactive tablet computer (6), is illustrated, which generates cognitive stimulation targeting the activation of the brain to perform cognitive activities such as reading, mathematical calculation, logic challenges, and emotional reactions such as happiness, and sadness.

Figure 4:
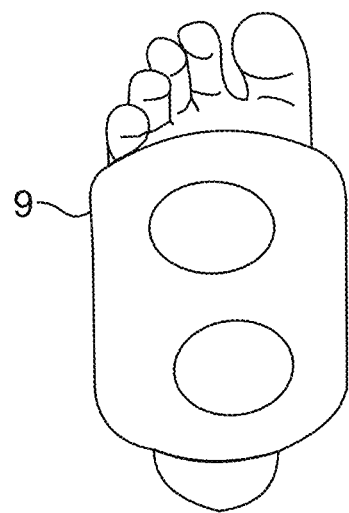
FIG. 4 is a schematic illustration of an example of mechanical stimulation of a patient's foot.

FIG. 4 illustrates a specific embodiment of mechanical stimulation to the foot of a patient. A wearable footwear device (9) is used to generate pressure or vibrations at specific locations of the foot, thereby stimulating nerves. The properties of the mechanical pressure or vibration stimuli, such as intensity, frequency and activation pattern are controlled wirelessly or via connection wires by the control unit (not shown in this drawing). This mechanical stimulation can be activated in time and intensity so that it is synchronized with other stimulation methods such as like electrical stimulation, or cognitive stimulation. The dual stimuli enhance the brain's response so that is greater than a reaction to a single stimulus.

Figure 5:
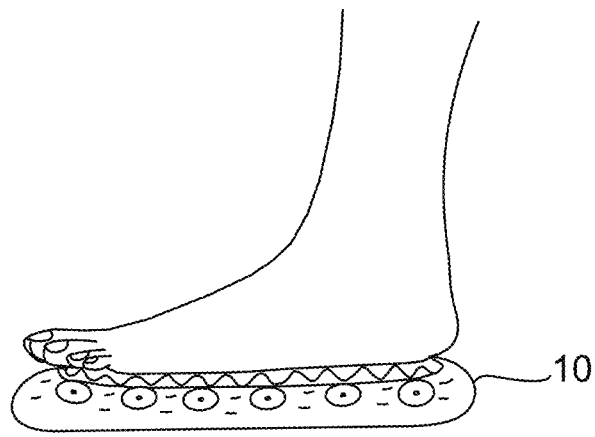
FIG. 5 is a schematic illustration of an example of thermal stimulation of a patient's foot.

FIG. 5 illustrates a specific embodiment of thermal stimulation to a foot of a patient. A thermal device (10) is used to generate heat or cold at specific locations of the foot to stimulate specific foot nerves. Specific requirements, such as the heating locations and temperature, are controlled wirelessly or via connection wires by a control unit (not shown in this Figure). The control unit can be integrated within the stimulation device (10). Thermal stimulation can be activated in time and intensity so that it is synchronized with other stimulation methods such as mechanical stimulation, electrical stimulation, or cognitive stimulation to produce a brain response greater than a reaction elicited by a single type of stimulation. The stimulation device (10) can be an integrated stimulation device that uses both thermal and mechanical (pressure or vibration) stimulations for greater therapeutic effect.

Figure 6:
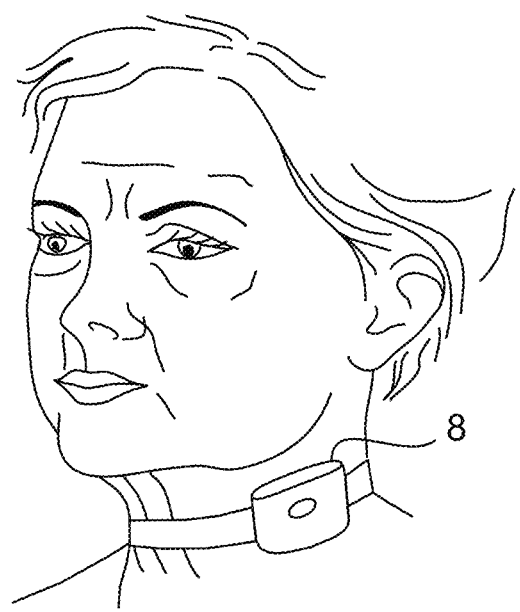
FIG. 6 is a schematic illustration of an example of mechanical stimulation of the carotid artery which in turn activates the carotid branch of the vagus nerve.

FIG. 6 illustrates another embodiment of the placement of a mechanical stimulator. The wearable vibrator (8), the stimulator, is positioned to be worn on the patient's neck. The stimulator generates mechanical vibration to stimulate the carotid artery, which in turn stimulates the carotid branch on the vagus nerve in the patient's neck. Properties of the mechanical vibration, such as intensity, frequency and pattern, are controlled wirelessly or via connection wires by the control unit (not shown in this Figure). The mechanical stimulation can be activated in time and intensity synchronization with other stimulators, such as electrical and thermal stimulators.

Figure 7:
FIG. 7 is a schematic illustration of an example of a wearable control unit.

FIG. 7 illustrates another embodiment of a wearable control unit (11) that is implemented as a watch. In this embodiment, the control unit (11) can control the stimulator wirelessly and can include an internal communication means to control implantable devices by placing the control unit near the implantable stimulator. This wireless control unit (11) can control one or more stimulators of the same type (electrical stimulators) or of different types (an electrical stimulator with mechanical stimulator).

With reference to FIG. 8, a simplified block diagram illustrates a stimulation optimization method based on feedback mechanism used with the systems described herein. One or more detectors (102) senses (111) the patient's (101) condition at a specific time and alerts (112) the controller (103) to activate (113) one or more stimulators (104) to alter the patient condition (114).

The patient (101) receives different stimulations (114) from different stimulators (104). The stimulators (104) can be one or more from the list of: electrical stimulator, mechanical (pressure or vibration) stimulator, cognitive stimulator (an interactive computer, tablet or smartphone), thermal stimulator (heat), audio stimulation, and more. A single stimulator of the same kind or more than one of the same kind may be applied.

A control unit (103) orchestrates the stimulation by defining timing, intensity and pattern of each stimulator (104) by direct communication (113) with each stimulator. Control unit (103) may be integrated with other parts of the system or stand alone. The communication (113 and 112) of the control unit may be wired to the system's stimulators and detectors or this could be affected in a wireless configuration.

The detectors (102) may include one or more detectors from the list of: brain activity detector like EEG, heart rate detector like ECG, breathing detector, motion detector, sleep detector, eye tracking detector, cognitive detector like tablet interacting with the patient, etc. Each specific detector or sensor (102) will sequentially measure attributes of the specific measured parameters and report (112) them directly to the control unit (103) to decide on the appropriate stimulation (114) by the dedicated stimulator (104).

The special close loop sensing and stimulation method illustrated in FIG. 8 enables various modes of operation like:

1. Stimulation in specific cognitive state of the patient, like: vagus nerve stimulation (114) by implanted vagus nerve stimulator (104) during REM sleep stage as detected by sleep sensor (102). This combination enhances the effect of the electrical vagus nerve stimulation as the brain is starving for neurotransmitters at REM sleep stage and the VNS may provide them.
2. Inducing a specific cognitive state, for example, sadness, by a cognitive stimulator (104) such as a sad movie. Then detecting the intensity of the cognitive state by a cognitive detector (102) and if the intensity is above a predetermined value, activating mechanical carotid stimulator (104) which affects the vagus nerve and induces an enhanced brain response.
3. A feedback mechanism in which a noninvasive electrical vagus nerve stimulation (104) is imposed to enhanced the patient memory. Control unit (103) receives (112) readings of an EEG sensor (102) reading that detect theta waves intensity (111) can adjust the stimulator (104) to enhance the stimulation affect and consolidate the memory of the patient in a more efficient way.
4. Closed loop adjustments in real time the stimulation (114) to the activity intensity as measured by specific detector (102). For example, controlling a thermal stimulator (104) to stabilize heart rate (HR) as measured (111) by an ECG sensor (102). In this case, the control unit (103) receives (112) frequent readings from HR (102) and dynamically adjusts (113) the thermal stimulator (104). The combined effect of the closed loop stimulation response teaches the patient to better control the HR under various conditions.
5. Combined synchronized stimulations from more than one stimulator (104) can enhance patient therapy. For example, the control unit (103) activates (113) sound stimulation (114) by an audio system (104) which can induce happiness in the patient and if at the same time or at some time delay (both herein denoted as synchronization) an electrical stimulator (104) is activated (113) so that the system can more effectively treat depression in the patient.
6. Pin pointing the most effective stimulation timing by combining readings (111) from more than one detector (102) may intensify the therapy effect of this stimulation. For example, a sleep detector (102) may provide a general time of a specific sleep stage, but combining it with an eye tracking sensor (102) will allow pin pointing the exact time of onset of REM stage sleep, which in turn is the most sensitive time for VNS stimulation (114) as the brain is starving for neurotransmitters at this time. VNS stimulation induces the brain to release neurotransmitters and at the onset of REM sleep it may intensify memory consolidation.

It should be noted that a combination of the stimulation control mechanisms can be used involving more than one sensor or detector enabling stimulation control based on a combination of body conditions, for example elevated heart rate (measured with ECG) while walking (measured with an activity sensor) or REM sleep (measured by a sleep detector combined with an EEG sensor).

Figure 9:
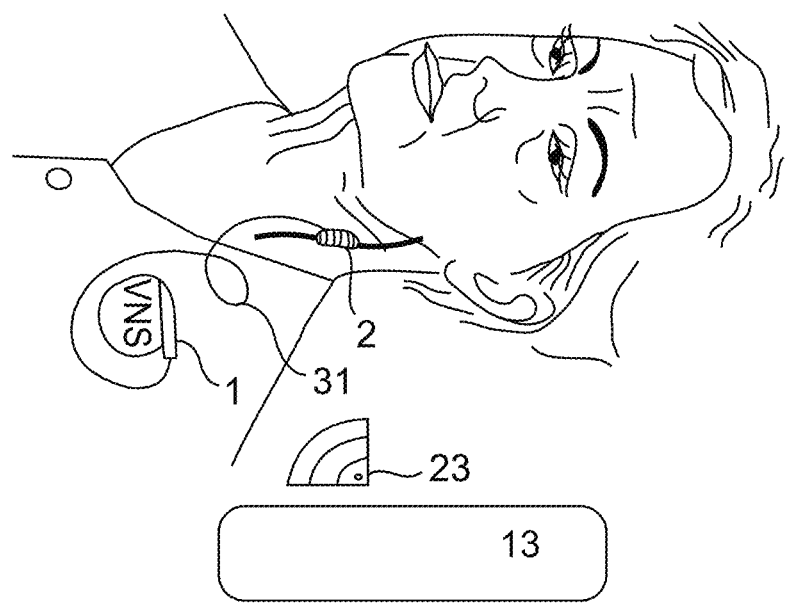
FIG. 9 is a schematic illustration of a second embodiment of the proposed system.

FIG. 9 depicts a schematic illustration of one embodiment of the proposed system which comprised of electrical stimulation by VNS using implantable stimulator (1), and sleep sensor (13) for triggering the stimulation. A patient has an implanted vagus nerve stimulation system (1) so that the vagus nerve electrode (2) is attached to the vagus nerve. The vagus nerve electrode is connected to the nerve stimulator (1) by a flexible lead (31). A sleep sensor unit (13) may be placed under the mattress, close to the nerve stimulator to enable wireless communication (23) between the control unit and the nerve stimulator. The control unit can be embedded in the sleep sensor (13) or separately located. The sleep sensor (13) can be placed in proximity of the implantable stimulator using a vest, a belt or a sticker. In addition, the control unit can control wirelessly or through wire communication one or more activation or monitoring means, like music player or heart rate recorder.

Figure 10:
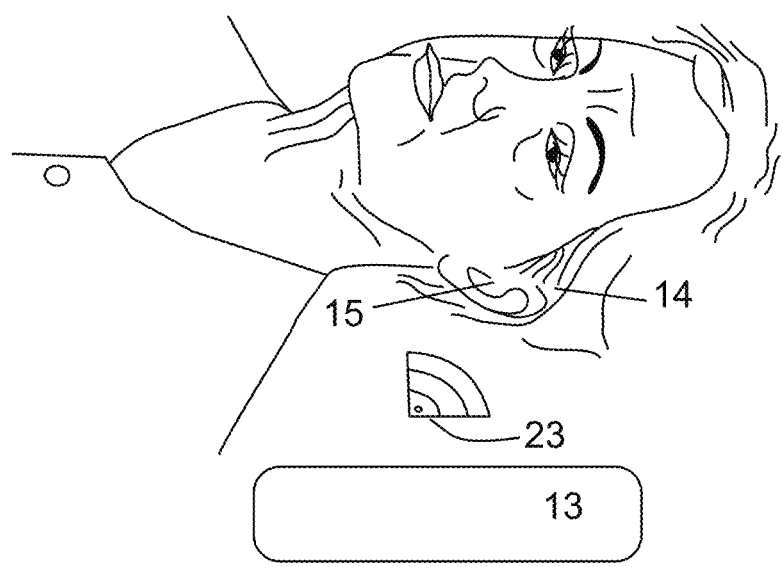
FIG. 10 is a schematic illustration of third embodiment of the proposed system.

FIG. 10 illustrates specific embodiment which comprised of electrical activation by tVNS using non-invasive ear stimulator (14) behind the ear, while electrode (15) is attached to external ear Concha or ear canal, and sleep sensor (13) for triggering the stimulation. A patient has a miniature system so that the vagus nerve electrode (15) is attached to the auricular branch of the vagus nerve. A sleep sensor unit (13) is placed under the mattress, close to the nerve stimulator to enable wireless communication (23) between the control unit which embedded in the sleep sensor (13) and the nerve stimulator.

FIGS. 11A to 11C illustrate other possible embodiments of the proposed tVNS electrode location where the ABVN presence or supply is prominent: like electrode attached to the Concha (16), or to the wall of the external ear canal (17), or attached to the back of the ear (18), or have its poles spilt between said locations, or attached to multiplied locations. The electrode shape will be such to maximize the tVNS efficiency per location.

FIG. 12 illustrates an embodiment of using a mask sleep sensor (19) with a tVNS stimulator integrated into it (20). In the Figure the tVNS electrode is shown as originating from the mask belt.

Figure 13:
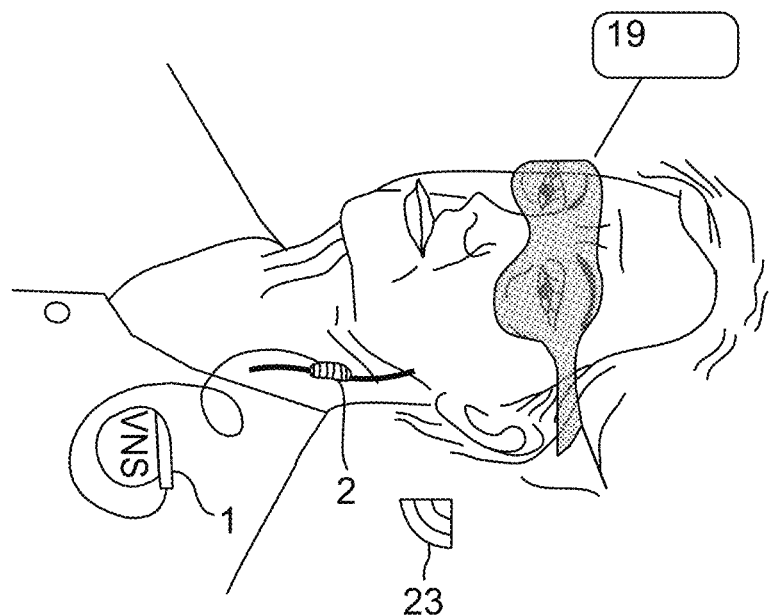
FIG. 13 is a schematic illustration of a fifth embodiment of the proposed system which is comprised of electrical activation by VNS using implantable stimulator and mask sleep sensor

FIG. 13 illustrates another specific embodiment of a mask sleep sensor (19) with the invasive VNS stimulator (1) is triggered by sleep mask (19) via Bluetooth communication (23).

Figure 14:
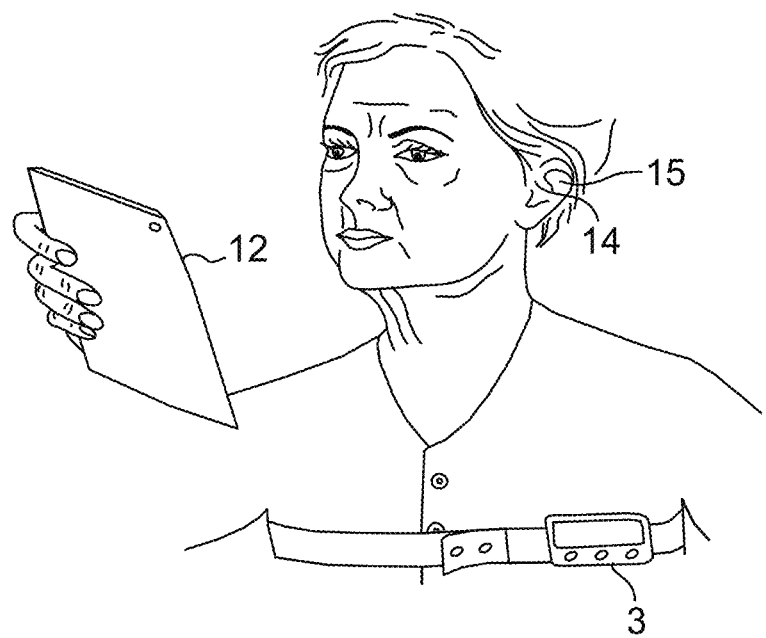
FIG. 14 is a schematic illustration of a sixth embodiment of the proposed system

FIG. 14 depicts a schematic illustration of yet another embodiment of the proposed system. The system provides electrical activation by tVNS using a non-invasive stimulator (14), an interactive tablet computer (12) for cognitive stimulation and cognitive detection, and a wearable control unit (3). The electrode (15) is attached to external ear Concha to stimulate the ABVN.

FIG. 15 depicts a schematic illustration of one embodiment of the proposed system. The Figure shows a completely-in-canal (CIC) type of device which is made of three units: a stimulating section (14) with electrodes (15), a wireless connection section (21) and a battery (22). The soft encapsulation (45) of device (41) has an arm (20) to assist with the insertion and removal of the device (41) from the ear canal.

FIG. 16 illustrates another embodiment which generates electrical activation by tVNS. The system comprises a non-invasive behind the ear stimulator (14) triggered by sleep sensor (13). The tVNS stimulator electrode (15) is attached to external ear concha or ear canal, so that the auricular branch of the vagus nerve is stimulated. The sleep sensor unit (13) is placed under the mattress, close to the nerve stimulator (14) to enable wireless communication (23, 24) between the control unit embedded in the sleep sensor (13) and the nerve stimulator (14). Sleep sensor (13) can be placed in proximity to the implantable stimulator using a vest, a belt or a sticker. The sleep sensor can control wirelessly one or more stimulators or monitors, such as a music player or a heart rate recorder.

Figure 17:
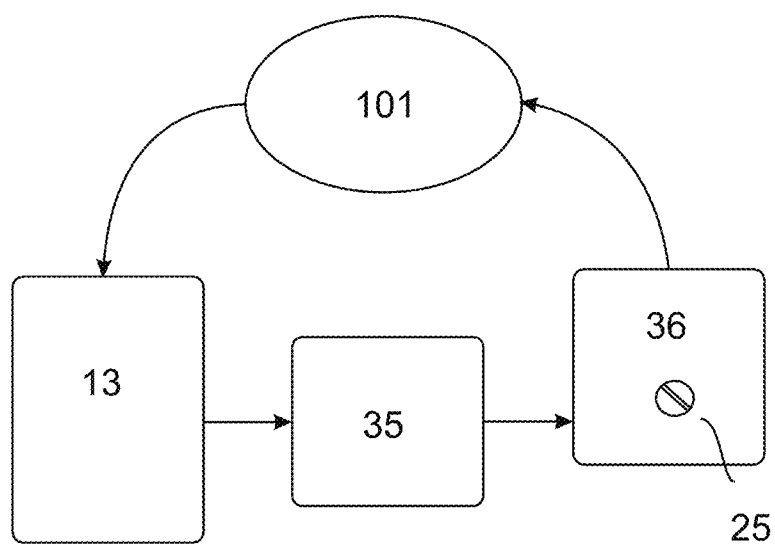
FIG. 17 illustrates a block diagram depicting how stimulation is activated or deactivated from the sleep sensor via wireless communication to the stimulator platform.

FIG. 17 depicts a block diagram where patient (101) stimulation is activated or deactivated by a stimulator platform (36) controlled by a control unit (35) based on sleep sensor (13). Detection is reported via wireless communication. Also shown is an electro-mechanical tuning screw head (25) which tunes the pulse amplitude or frequency of the stimulator based on the patient's reported comfort level.

Figure 18:
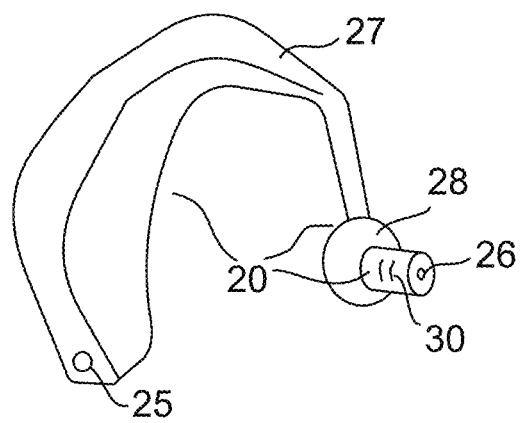
FIG. 18 depicts a behind-the-ear stimulation device.

FIG. 18 shows an exemplary behind-the-ear tVNS stimulation device (27), within a soft material encapsulating (20) body. The electrodes contact (30) is placed on the ear canal wall. A hole (26) allows minimal sound blockage and pressure balancing. The electrode base (28) fits the ear concha to allow for patient comfort and the mechanical stability of the device. Also shown is an electro-mechanical tuning screw head (25) to modify the pulse amplitude based on the reported comfort of the patient. Ear stimulator (27) may also incorporate an audio stimulator which will activate a speaker within the hole (26). The audio stimulator will be activated in synchronization with the tVNS electrical stimulator to enhance the combined therapeutic effect.

FIG. 19 depicts an in-the-ear type tVNS stimulation device, with a hole (26) in its body to allow minimal sound blockage and pressure equalization. The device body base (28) is shaped to fit the ear concha to allow patient comfort and the mechanical stability of the device.

Figure 20:
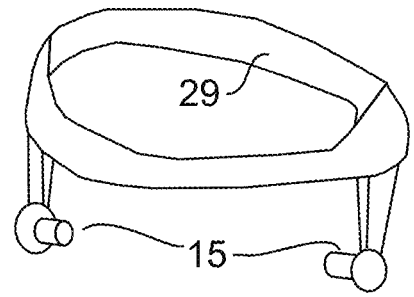
FIG. 20 depicts a band holding two stimulation means for positioning electrodes in both ears.

FIG. 20 depicts a headband containing a tVNS simulation device, and potentially a sleep sensor with electrodes (15) placed in both ears. Electrodes (15) can be used for both sensing and stimulation. The electrodes are connected and measure the electrical potential difference between the two ears for basic EEG analysis. For these functions and additionally for mechanical stability, a supporting band (29) is place at the back of the head and at the forehead.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A neuromodulation system for treatment of physiological disorders comprising:
    at least one non-invasive vagus nerve stimulator comprising at least one electrode for stimulating a cranial nerve, wherein said at least one electrode is configured to be mounted on a head of a subject and stimulate a vagus nerve;
    a sleep sensor configured to measure signals indicating at least one sleep stage in said subject;
    one or more brain activity detectors configured to measure brain activity of a subject by measuring changes in EEG theta waves; and
    a control unit, wherein said control unit determines that said subject is in said at least one sleep stage based on signals from said sleep sensor, and controls stimulation during said at least one sleep stage by the at least one non-invasive vagus nerve stimulator via said at least one electrode to enhance stimulation effect during said sleep stage based on changes in said EEG theta waves measured by said one or more brain activity detectors during said at least one sleep stage.

2. A system according to claim 1, wherein said at least one electrode is configured to be placed in at least one of, in at least one of, a back of an ear, a concha and/or an ear canal, and stimulate an auricular branch of the vagus nerve.

3. A system according to claim 1, wherein said one or more brain activity detectors are configured to measure signals indicating changes in hippocampus activity, and wherein said control unit controls stimulation by the at least one non-invasive vagus nerve stimulator via said at least one electrode based on said signals indicating said changes in hippocampus activity.

4. A system according to claim 3, wherein said changes in hippocampus activity indicate at least one sleep stage, and wherein said control unit activates said at least one non-invasive vagus nerve stimulator to deliver aid stimulation during said at least one sleep stage based on said measured signals indicating said changes in hippocampus activity.

5. A system according to claim 1, wherein said control unit is configured to determine a functional status of an attention deficit disorder (ADD) or of an attention deficit and hyperactivity disorder (ADHD) in a subject based on said signals measured by said one or more brain activity detectors, and to control said stimulation by the at least one non-invasive vagus nerve stimulator based on said determined functional status.

6. A system according to claim 5, wherein said control unit adjusts parameters of said stimulation based on said determined functional status.

7. A system according to claim 1, wherein the control unit is configured to provide a feedback mechanism that controls the at least one non-invasive vagus nerve stimulator, and wherein the feedback mechanism is feedback based on a cognitive result and/or the measured brain activity.

8. A system according to claim 1, wherein said one or more brain activity detectors comprises an EEG detector.

9. A system according to claim 1, wherein said at least one electrode comprises at least two electrodes.

10. A method for vagus nerve stimulation, the method comprising:
    determining that a subject is in at least one sleep stage based on signals received from at least one sleep sensor;
    measuring during said at least one sleep stage, changes in EEG Theta waves of said subject using one or more brain activity detectors of a neuromodulation system;
    applying stimulation to a vagus nerve by at least one electrode of a vagus nerve stimulator of said neuromodulation system placed in at least one of, a back of an ear, a concha, and/or an ear canal; wherein said applying comprises applying said stimulation to said vagus nerve to enhance an effect of said stimulation according to said changes in EEG Theta waves measured during said determined at least one sleep stage.

11. A method according to claim 10, comprising:
    detecting changes in hippocampus activity based on said measured brain activity, and wherein said applying comprises applying said stimulation based on said detected changes.

12. A method according to claim 11, comprising determining at least one sleep stage based on said changes in hippocampus activity, and wherein said applying comprises applying said stimulation based on said determined sleep stage.

13. A method according to claim 10, comprising determining a functional state of an attention deficit disorder (ADD) or of an attention deficit and hyperactivity disorder (ADHD) in said subject based on said measured brain activity, and wherein said applying comprises applying said stimulation to said vagus nerve according to said determined functional state.

14. A method according to claim 10, comprising performing said measuring and said applying during sleep.

15. A method according to claim 10, wherein said applying comprises applying said stimulation together with cognitive stimulation of the brain.

16. A method according to claim 10, comprising performing said measuring and said applying while the subject is physically active.

17. A vagus nerve stimulation method, comprising:
    applying stimulation to a vagus nerve by at least one electrode mounted on a head of the subject;
    providing simultaneously with said applying, additional cognitive stimulation to the subject, wherein said additional cognitive stimulation comprises audio stimulation.

18. The method of claim 17, wherein said additional cognitive stimulation comprises at least one of, a cognitive challenge, and/or an emotional challenge.

19. The method of claim 17, wherein said additional cognitive stimulation comprises one or more of, mathematical problems, memory challenges, verbal tasks, and visual tests.

20. The method of claim 17, wherein said subject is a subject having at least one of, cognitive decline, Amnestic Mild Cognitive Impairment (AMCI), Dementia, Alzheimer, Parkinson and/or Tremor.

21. The method of claim 17, comprising detecting intensity of cognitive activity, and wherein said applying comprises applying said stimulation during a period of high cognitive activity based on the results of said detecting.

22. The method of claim 17, wherein said applying comprises applying said stimulation by at least one electrode placed in at least one of, a back of an ear, a concha, and/or an ear canal.

* * * * *